(12) United States Patent
Aper et al.

(10) Patent No.: US 11,065,366 B2
(45) Date of Patent: Jul. 20, 2021

(54) METHOD FOR PRODUCING A FIBRIN-BASED BIOARTIFICIAL, PRIMARILY ACELLULAR CONSTRUCT, AND THE CONSTRUCT ITSELF

(71) Applicant: MEDIZINISCHE HOCHSCHULE HANNOVER, Hannover (DE)

(72) Inventors: Thomas Aper, Hannover (DE); Mathias Wilhelmi, Isernhagen (DE); Axel Haverich, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 0 days.

(21) Appl. No.: 15/740,247

(22) PCT Filed: Jul. 7, 2016

(86) PCT No.: PCT/EP2016/066135
§ 371 (c)(1),
(2) Date: Dec. 27, 2017

(87) PCT Pub. No.: WO2017/005857
PCT Pub. Date: Jan. 12, 2017

(65) Prior Publication Data
US 2018/0200404 A1 Jul. 19, 2018

(30) Foreign Application Priority Data
Jul. 9, 2015 (DE) .................... 10 2015 111 126.8

(51) Int. Cl.
*A61L 27/26* (2006.01)
*A61L 31/04* (2006.01)
(Continued)

(52) U.S. Cl.
CPC ............ *A61L 27/26* (2013.01); *A61L 27/225* (2013.01); *A61L 27/507* (2013.01); *A61L 27/54* (2013.01);
(Continued)

(58) Field of Classification Search
CPC ......... A61L 2300/236; A61L 2300/252; A61L 2300/254; A61L 2300/418; A61L 2300/42;
(Continued)

(56) References Cited

U.S. PATENT DOCUMENTS

| 3,425,561 | A | * | 2/1969 | Steele | B04B 7/18 210/380.1 |
| 3,723,244 | A | * | 3/1973 | Breillatt, Jr. | A61L 27/225 162/151 |
| 2002/0168398 | A1 | * | 11/2002 | Delmotte | A61L 27/225 424/443 |

FOREIGN PATENT DOCUMENTS

| DE | 695 27 899 T2 | 3/2003 |
| DE | 602 22 543 T2 | 6/2008 |

(Continued)

OTHER PUBLICATIONS

Aper et al., "Fibrinogen Preparations for Tissue Engineering Approaches", Journal of Bioengineering and Biomedical Sciences, Jan. 1, 2012, vol. 2, No. 3.
(Continued)

*Primary Examiner* — Michael B. Pallay
(74) *Attorney, Agent, or Firm* — W & C IP (57) ABSTRACT

The invention relates to a method for producing a bioartificial and primarily acellular fibrin-based construct, wherein a mixture of cell-free compositions containing fibrinogen and thrombin is applied to a surface and subsequently pressurised. An additional aspect of the invention is directed to such fibrin-based bioartificial acellular constructs
(Continued)

obtained according to the invention, with improved biomechanical properties, as well as to the use of same in the field of implantology, cartilage replacement or tissue replacement.

13 Claims, 6 Drawing Sheets

(51) Int. Cl.
  *A61L 27/22*   (2006.01)
  *A61L 27/50*   (2006.01)
  *A61L 27/54*   (2006.01)
  *A61L 33/00*   (2006.01)
  *A61L 33/08*   (2006.01)

(52) U.S. Cl.
  CPC ......... *A61L 31/046* (2013.01); *A61L 33/0011* (2013.01); *A61L 33/08* (2013.01); *A61L 2300/236* (2013.01); *A61L 2300/252* (2013.01); *A61L 2300/254* (2013.01); *A61L 2300/418* (2013.01); *A61L 2300/42* (2013.01); *A61L 2420/02* (2013.01); *A61L 2430/06* (2013.01); *A61L 2430/20* (2013.01)

(58) Field of Classification Search
  CPC ............. A61L 2420/02; A61L 2430/06; A61L 2430/20; A61L 27/225; A61L 27/26; A61L 27/507; A61L 27/54; A61L 31/046; A61L 33/0011; A61L 33/08; B04B 7/18
  See application file for complete search history.

(56) References Cited

FOREIGN PATENT DOCUMENTS

| | | |
|---|---|---|
| WO | 03/035115 A2 | 5/2003 |
| WO | 2013/091865 A1 | 6/2013 |

OTHER PUBLICATIONS

Aper et al., "Engineering of small diametric tubular compacted fibrin matrices", Bionanomat, Jan. 1, 2016, pp. 13-17, vol. 17.

\* cited by examiner

METHOD FOR PRODUCING A FIBRIN-BASED BIOARTIFICIAL, PRIMARILY ACELLULAR CONSTRUCT, AND THE CONSTRUCT ITSELF

The present invention relates to a method for producing a fibrin-based bioartificial and primarily acellular fibrin-based construct, wherein a mixture of fibrinogen-containing and thrombin-containing cell-free compositions is applied to a surface and then pressurised. In a further aspect, the present invention relates to such acellular fibrin-based constructs with improved biomechanical properties obtained according to the invention and to their use in the field of implantology, cartilage replacement or tissue replacement.

PRIOR ART

The field of tissue engineering, and more particularly, the use of tissue engineering in medical transplantation technology, is becoming increasingly important in patient care. In this field, the production of artificial, biological (tissue) constructs that can be used in medical transplantation technology is playing an increasingly significant role.

For over 30 years, efforts have been in progress in the field of tissue engineering to replace the body's own materials, such as organs, blood vessels or tissue patches, with artificial tissue constructs produced in the laboratory of biological materials and optionally the body's own materials that are to the extent possible of equivalent quality and can be used as medical transplants. The most frequent approaches are those in which tissue constructs are provided that are generated in vitro in such a way that they can be introduced into the body as functional implants, ordinarily along with cells. This means that the tissues are already fully colonised with corresponding cells and differentiated, so that generation of the tissue takes place fully in vitro and this tissue construct is them implanted. There is a great need to provide suitable bioartificial constructs that must meet the widest possible range of requirements. They must not cause any undesired reactions in the body, such as rejection reactions and the like. This means that the biocompatibility of the constructs, and if applicable their hemocompatibility, is of primary importance. To the extent possible, the artificial construct must be accepted by the body in such a way that it is not recognized as foreign and no pathological reactions are triggered.

In addition, one must also differentiate between constructs having a matrix that is to remain in the body permanently and those having a matrix that dissolves in the body over time.

In this connection, tissue constructs are ordinarily understood as a product that is formed from a matrix material and from differentiated and/or undifferentiated cells, wherein this formation takes place in vitro. Attempts are currently in progress to use such bioartificial tissue constructs as a replacement for synthetic materials. In this case, a natural biological material is used as a matrix material, e.g. extracellular matrices such as those occurring in nature. Such materials are desirable because they are correspondingly well-tolerated in the body.

Alternatively, permanent structures in the tissue construct can be used as matrices, such as synthetic structures including plastic structures or metal structures. These structures permanently remain in the body, or if applicable, must be removed in a second operation.

A widely differing variety of methods for generating bioartificial tissue constructs is known from the prior art. By way of example, reference is made here to WO 2013/091865 A1, which describes a method and a device for producing bioartificial tissue constructs with the aid of a rotational method. In this case, bioartificial tissue constructs are produced in which cell-matrix composites are produced. Here, the cells are directly used for in situ generation of the tissue construct. In most methods for producing corresponding tissue constructs, the cells must be first be placed in or on the matrix in vitro and then optionally cultivated in order to form a tissue construct. This construct is then implanted in the body.

A problem of such tissue constructs is that they are usually manufactured in individual production for direct application. This means that in a first step, cells are removed from the patient, and they are then cultivated for a specified period of time in or on the matrix. After in vitro generation of the tissue construct, this construct is implanted in the body of the recipient. Such methods require extensive measures and complex facilities. Furthermore, such methods and the generation of such constructs require extensive approval procedures that make their use more difficult. For this reason, there is a need to provide new methods allowing the generation of bioartificial constructs that can be safely and quickly produced, show outstanding storage stability, and whose use does not require the fulfillment of complex and unique approval requirements.

Another aim of the present invention is to provide constructs that can also replicate more complex structures. The structures described in WO 2013/091 865 A1 are hollow bodies that can be used as corresponding hollow bodies, but for the formation of other structures, the hollow body must be cut and remodeled to form the corresponding desired structures. In this case, however, these produced tissue constructs are subjected to new forces that can impair their mechanical properties.

Accordingly, a further object of the present invention is the provision of constructs with improved mechanical properties.

Provided in order to achieve these objects are a method, corresponding constructs, and use thereof.

DESCRIPTION OF THE INVENTION

The method according to the invention is a method for producing a fibrin-based bioartificial and acellular construct comprising the following steps:

- provision of a fibrinogen-containing and cell-free composition;
- provision of a thrombin-containing and cell-free composition;
- application of the fibrinogen-containing cell-free and thrombin-containing cell-free compositions to a surface;
- pressurisation of the mixture of compositions applied to the surface at least until the fibrin formation is essentially completed; and
- removal of the fibrin-based acellular bioartificial construct from the surface.

According to the invention, the term "bioartificial and acellular fibrin-based construct" is understood to be a construct primarily containing no cells. This means that no cells are introduced into the construct during the production method. This construct is fibrin-based, i.e. the matrix of the construct is essentially a fibrin matrix or comprises a layer that is essentially a fibrin matrix.

The term "matrix" is understood to mean a supporting structure composed of fibrin. Here, the matrix is a provisional matrix (which means that it dissolves after implantation) that forms a supporting framework and imparts to the construct the corresponding mechanical strength.

In addition to the matrix composed of fibrin, the construct can also comprise further layers or other non-cellular components.

In the present application, the terms "cell-free" and "acellular" are used as synonyms.

In the present method, a fibrinogen-containing and cell-free composition is provided, a thrombin-containing and cell-free composition is provided, and these compositions are applied to a surface of a substrate.

In an embodiment, the fibrinogen-containing composition is obtained from plasma by conventional methods. Such methods include cryoprecipitation or ethanol precipitation. In this case, the plasma may originate from the recipient of the future construct according to the invention or may be allogeneic or xenogeneic fibrinogen or plasma. Optionally, the fibrinogen-containing composition can first be subjected to washing and/or purification steps, for example in order to separate out other components such as fats or albumins. The composition can also comprise synthetic or recombinant fibrinogen.

In an embodiment, the separated fibrinogen is resuspended from the plasma in such a way that the concentration of the fibrinogen is at most 60 mg/ml, such as at most 50 mg/ml, e.g. at most 20 mg/ml. In an embodiment, the concentration of the fibrinogen in the fibrinogen-containing composition is adjusted such that it is in the range of 10 to at most 20 mg/ml. The resuspension can e.g. be carried out with the plasma. For example, 8 to 10 ml of fibrin preparation are obtained from 50 ml of plasma.

In an embodiment, fibrinogen in this case is relatively strongly diluted, and the solution is highly aqueous and is favourably distributed on the substrate. The low concentration causes cross-linking of the fibrinogen to take place slowly.

The thrombin-containing composition is a thrombin-containing solution in an embodiment that contains the thrombin in an amount of 100-1000 units per ml. As a solvent, for example, one can use water for injection. Suitable solvents for both the fibrinogen-containing composition and the thrombin-containing composition are known to the person skilled in the art.

In an embodiment, in use of a relatively highly diluted fibrinogen solution, such as a fibrinogen-containing solution with a fibrinogen concentration of at most 20 mg/ml, a thrombin solution is added in advance so that the ratio of thrombin (units per ml) to fibrinogen (mg per ml) is in a range of 1:1 to 10:1.

After application of the fibrinogen-containing acellular composition and the thrombin-containing acellular composition to a surface, the mixture of compositions applied to the surface is pressurised. This pressurisation, which can be carried out immediately after application of the compositions, but also not until a predetermined point in time, is carried out at least until the fibrin formation is essentially completed. This should be completed within a period of at most 30 to 45 min and depends on the mixing ratio and concentration of the reactants, fibrinogen and thrombin.

This means that pressurisation takes place such that polymerisation of fibrinogen via the thrombin for the formation of fibrinogen at least partially takes place under pressure. Fibrin is the polymerised fibrinogen that is cross-linked by means of the thrombin. Fibrils are formed, which result in fibrin fibers. In this case, the three-dimensional structure of a fibrin matrix is formed.

It is presumed that because of the pressurisation, the fibrinogen structures are brought closer to one another, so that improved and strengthened cross-linking of the fibrinogen to the fibrin can take place. In this manner, improved mechanical properties of this fibrin structure can be achieved. The fibrils of the fibrinogen are brought into closer contact, and stronger cross-linking takes place between the fibrils. This fibrin matrix, which is compressed compared to a non-pressurised fibrin matrix, shows higher stability with respect to shearing and pressurisation. The risk of damage to this structure in a construct inserted into the body is reduced. A problem with the currently produced tissue constructs, more particularly those subjected to intense mechanical loads such as vascular grafts or cartilage, is their low stability in this type of use. Accordingly, attempts have been made in the prior art to stabilise such tissue constructs by in vitro cultivation with corresponding cells in order to then implant them as tissue constructs.

It has now been found that by means of corresponding pressurisation, fibrin matrices are achieved that can be used as fibrin-based bioartificial and acellular constructs for implants.

In addition to their improved mechanical properties, these constructs also show improved storage capacity. Because these constructs do not contain any cells, outstanding storage stability can be achieved. It is even possible to correspondingly produce cryopreserved constructs by freeze-drying. It has been found that the constructs according to the invention can be stored in the refrigerator in a corresponding preservative medium for least two months. It has further been found that bioartificial and acellular constructs obtained in this manner can be subjected to cryopreservation, which further increases their storage capacity. These constructs can be stored for over six months.

Because of their favourable shelf life and stability during storage, these constructs can be supplied quickly. As the constructs are acellular, they can be used independently of the individual in question. In contrast to cellular constructs, which require individual in vitro production, the constructs according to the invention can be stored and quickly used.

In an embodiment, pressurisation of the mixture applied to the surface is effected by introducing this mixture into a rotating hollow body (rotating mould), so that compositions are distributed and spread out on the surface of the hollow body. In an embodiment, the strong dilution of the fibrinogen preparation allows outstanding distribution of the compositions in the rotating mould. The pressurisation takes place in the mould due to centrifugal forces produced by rotation of the hollow body.

A rotational method for producing a tissue construct is described for example in WO 2013/091865 A1. In this case, however, a matrix material such as fibrinogen together with cells is introduced into the rotating hollow mould with the aid of an applicator in the form of a lancet, wherein the applicator is displaced along the rotational axis during introduction. The method according to the invention relates to the method of producing an acellular construct, i.e., the introduced compositions are cell-free.

In a further embodiment, displacement of the applicator along the axis of rotation is not necessary, because the fibrinogen-containing composition and the thrombin-containing composition are highly aqueous, either alone or as a mixture, and are quite favourably distributed in the rotating mould. Application can also be carried out at one end of the rotating mould, in which case the mixture is uniformly distributed in the rotating mould while this mixture is cured by polymerisation.

Introduction of the reactants and formation of the fibrins takes place in an embodiment such that there is a force at the surface of the hollow body of at least 600 g, such as, for example, at least 800 g, e.g. at least 900 g.

In the conventional rotational method, in which cells were simultaneously introduced, only quite low g forces could be used because of the presence of the cells. For example, WO 2013/091865 A1 describes introduction of the cells during rotation at between 100 g and 600 g. In the examples in this case, g forces of 150 and 330 g were mentioned. The same applies to pressurisation in general.

According to the invention, when pressurisation is carried out by rotation, significantly higher pressurisation due to centrifugal force can be carried out, specifically of at least 600 g, such as at least 800 g, at least 900 g, e.g. at least 1000 g. In this manner, substantially improved mechanical properties can be achieved.

In a further embodiment, pressure can be applied in planar fashion to the surface composition. This planar pressurisation allows the formation of more complex constructs. This means that more complex structures having individual geometries can be formed accordingly. In this case, a substrate of the desired shape is provided, and the compositions are applied to the surface of this substrate. Compared to the rotational method, the advantage of formation of the planar products based on the provided substrate is that this allows not only the formation of corresponding tubular constructs, but also the possibility of providing other geometries. The widest possible variety of geometries can be configured, with essentially any form being conceivable in this case, including undercut areas.

It is therefore possible for the structures produced in this manner to show the desired mechanical properties, which were impaired in the case of formation of simple structures on a surface or structures produced in the rotational method due to modification of the construct, such as cutting open or cutting up the structure and adaptation to a three-dimensional mould.

In an embodiment, application of pressure in planar fashion to the surface compositions is carried out with a relative pressure of at least 1 bar, such as at least 5 bar, at least 10 bar, or at least 15 bar.

It is possible using the methods according to the invention to provide constructs with wall thicknesses of more than 1 mm, such as 1.5 mm and thicker, for example more than 2 mm. Such layers are not described in the prior art. It was ordinarily possible to apply layers of at most 0.5 mm. The methods according to the invention thus advantageously allow the provision of bioartificial, acellular constructs of increased layer thicknesses.

According to the invention, in a further step, a fibrin-based acellular bioartificial construct obtained in this manner is removed from the surface.

Accordingly, the surface can be configured such that removal is simple. In this case, for example, one can use a Teflon surface or other suitable known surfaces.

In an embodiment, it is possible according to the invention for the compositions, the fibrinogen-containing composition and the thrombin-containing composition, to be applied multiple times, either together or separately.

This makes it possible to obtain high thicknesses of the construct.

The method includes embodiments in which a plurality of layers is applied. These layers may be identical layers. Alternatively, the fibrin-based constructs can also comprise other non-fibrin-containing layers.

In an embodiment, the uppermost layer produced in the method can be a heparin-containing layer. For this purpose, according to the invention, a thrombin-containing composition is applied as the uppermost layer, followed by a heparin-containing composition. The corresponding compositions are known to the person skilled in the art. Thrombin possesses binding sites for both fibrin and heparin. By applying heparin in the last step of the production process, the heparin is bound to the surface via the thrombin.

The formation of this heparin-containing layer makes it possible to prevent clotting in use of the construct according to the invention as a vascular graft.

Furthermore, layers can be present in the construct that are non-fibrin-containing layers, and such non-fibrin-containing layers can be composed of other biological materials that are cell-free or synthetic materials. These materials include biological materials, such as other components of the extracellular matrix, e.g. collagen, synthetic biocompatible materials such as polymers, ceramics or metals, as well as hybrids thereof. The introduction of active substances can also be advantageous in this case, such as selective growth factors, antimicrobial substances or mediators such as cytokines.

Here, this non-fibrin-containing layer can be arranged between fibrin-containing layers or on one or both sides thereof. It is presumed in this case that because of the incomplete formation of fibrin between the layers, whether between fibrin-containing layers or between fibrin-containing and non-fibrin-containing layers, a connection will take place such that the layers will engage with one another.

According to the invention, the applied layers have a thickness after pressurisation of at least 0.5 mm, such as at least 1 mm, e.g. at least 1.5 mm, for example at least 2 mm.

In an embodiment, the fibrinogen is fibrinogen isolated from plasma. In a further embodiment, the thrombin is thrombin isolated from the same amount of plasma.

The fibrinogen and/or thrombin used in this case can be an autologous, allogeneic or xenogeneic material. Preferably, autologous or allogeneic material is used in order to prevent possible reactions in the body of the recipient.

The method according to the invention allows the provision of bioartificial, acellular constructs, wherein this production is faster and simpler than methods in which cells are already integrated during the production process. Because of this cell-free operation, it is further possible to configure matrix structures in the construct such that they can be exposed to a substantially greater mechanical load in order thus to improve the biomechanical properties of the construct. It is presumed that this is possible because of the far greater compression of the fibrin matrix.

This thus allows use during surgery in which acellular autologous material is isolated from the patient, the construct is produced according to the invention and it is then immediately introduced into the recipient.

Furthermore, as there is no primary use of cells, the production method as a whole is simpler, and the corresponding matrices can be more strongly compressed than would be possible if cells were contained therein. Under the high forces that can occur according to the invention, cells would be subject to the risk of damage or death.

The construct obtained with this fibrin matrix further shows substantially improved biomechanical properties compared to the known tissue constructs. This applies both to shearing forces and to other forces acting on the construct.

With the aid of the method according to the invention, it is therefore also possible to provide constructs that can be used in tissues subjected to strong biomechanical forces, such as, for example, cartilage or cardiac valve leaflets.

This primary dispensing with cells further makes it possible to provide a construct with better storage properties. In fact, it was found that in addition to the known storage in conventional storage media, such as glutaraldehyde, the constructs according to the invention can also be freeze-dried. By means of dehydration during production, and more particularly, freeze-drying or cryopreservation, the matrix can be configured to be stable in storage. The constructs also show the desired stability after storage.

Furthermore, the method of freeze-drying not only allows theoretically unlimited and uncomplicated storage capacity, but it can also be presumed that this method will simultaneously provide even better biomechanical load capacity because of the accompanying removal of water.

In addition, constructs can be provided that can be correspondingly "adapted" with respect to their desired size. Because of the favourable storage capacity and simple production, it is possible to provide a continuous material that can be adapted according to the requirements.

In addition, the method according to the invention allows the provision of constructs with greater wall thickness, which accordingly leads to improved biomechanical properties.

According to the invention, by varying the degree of pressurisation in applying multiple layers of a construct composed of multiple layers, it is also possible to impart to said layers different mechanical properties. By varying the strength of compression and the composition of the components, correspondingly different properties of the layers of a construct can be generated.

According to the invention, further non-cellular components and substances can be added during the method, which are then integrated into the construct or are present on the surface of the construct. Such substances can be plasma components, and they can be used as autologous and/or allogeneic or xenogeneic and/or synthetic plasma components. Furthermore, additional stabilising substances, for example of autologous, allogeneic, xenogeneic or synthetic origin, can be used to further modify biomechanical properties.

Other substances can also be used, for example in order to prevent/alleviate infections or promote tissue characteristics such as growth induction, regeneration, etc. In the past, the use of these substances was only possible to a limited degree, because such substances can possibly have toxic effects on the tissues present on the tissue construct.

Furthermore, the construct according to the invention can contain other substances for improving tissue characteristics, such as e.g. heparin, growth factors or antimicrobial substances, but also toxic substances.

In an embodiment, the method is carried out with pressurisation by rotation in such a manner that the compositions are introduced into the system by rotation with the aid of an applicator in a fixed position. They are evenly distributed on the walls and polymerise out. In an alternative, the applicator is arranged in a moveable manner in the mould, so that the fibrinogen and thrombin solutions can be applied by moving them in and out. In the case, the two solutions can be brought into contact with each other and mixed at as late a stage as possible so that the reaction does not occur until application.

In this case, in an embodiment of the method according to the invention, no liquid is removed from the system during a first period. This period is at most 5 min, such as at most 3 min, e.g. at most 2 min after introducing the compositions. The excess liquid is then removed.

In another embodiment, the mould has through holes through which liquid can be discharged. These through holes, for example with a diameter of 0.1 mm to 1 mm, are sealed in an embodiment with a semipermeable material, preferably on the outside of the mould. This semipermeable material allows the separation of liquid, while the fibrinogen, the thrombin and the fibrin formed remain in the mould. This drainage makes it possible to remove a sufficient amount of liquid and impart to the construct the necessary stability.

In a further aspect according to the invention, a bioartificial, acellular fibrin-based construct can be obtained by means of the method according to the invention. This acellular, bioartificial construct that is obtainable with the aid of the method according to the invention shows a wide range of advantages over known tissue constructs:

The construct according to the invention shows outstanding biomechanical properties, so that it can also be used in tissues under high loads, such as cartilage or cardiac valve leaflets.

As cells can be dispensed with, the constructs show improved storage capacity, and more particularly, the construct can be freeze-dried. According to the invention, therefore, freeze-dried bioartificial, acellular fibrin-based constructs can be provided. According to an embodiment of the invention, the method according to the invention thus further comprises the step of freeze-drying of the obtained construct.

The construct is significantly simpler to produce, and because cells are dispensed with, the production thereof, as well as its use under approval conditions, is substantially simplified. In particular, the fibrin-based construct according to the invention allows length and diameter to be individually selected. Pre-manufactured constructs can be provided as medicinal products and can then be used in the recipient in an individually-adapted manner.

The construct according to the invention is characterized by a higher degree of compression than conventional tissue constructs, which improves its biomechanical properties.

Furthermore, constructs can be prepared having a substantially greater thickness, for example a hollow body with a wall thickness of >2 mm. In addition, the constructs according to the invention may also comprise coatings, such as heparin coatings, that hinder the formation of thrombi.

The bioartificial, acellular constructs according to the invention can thus comprise individualized forms of widely varying geometries.

In addition, it was surprisingly found that when such constructs are used as a vascular graft, they show at least equally favourable properties to vascular grafts generated in vitro, which contain corresponding cells present in the vessel, such as smooth muscle cells, endothelial cells, etc. In fact it was found that the vascular grafts can also be used without cells and are capable of germinating cells and forming corresponding structures. In this case, this formation takes place in such a way that the structures have the same structure as those occurring naturally, for example in the case of blood vessels, structures having a corresponding arrangement of endothelial cells, smooth muscle cells, etc. The germination of the cells proceeds from the outside to the inside, but the diameter of the blood vessels is not restricted. This means that the cells grow from the surrounding tissues into the constructs, but not into the lumen of the hollow body. It was found that six weeks after implantation, the constructs according to the invention were no longer distinguishable from normal vessel structures. The fibrin of the structure could no longer be detected after a few months, showing that the constructs according to the invention are fully degraded after implantation.

Here, the constructs according to the invention can be configured as a patch or a tubular body, depending on the production method.

These constructs according to the invention can be used in tissue engineering, e.g. also for in vitro pre-conditioning. For example, use as a cartilage replacement is possible, i.e. small pieces of the fibrin construct are introduced into the relevant areas of the body, resulting in in vivo colonisation by chondrocytes and chondroblasts.

In addition to vascular grafts, further areas of application of the bioartificial, acellular fibrin-based constructs according to the invention include all types of implants, such as cartilage replacement, but also as a matrix for in vitro production. In addition, the constructs according to the invention can also be used for tissues subjected to heavy biomechanical loads, such as cartilage or cardiac valve leaflets.

In an embodiment, the bioartificial, acellular fibrin-based construct can be obtained using autologous materials.

Finally, the application is directed to the use of the bioartificial, acellular constructs according to the invention as an implant, cartilage replacement, matrix for in vitro production of tissue replacement or vascular graft, as well as for cardiac valve leaflets and tissues for the reconstruction of cardiovascular structures such as the atrial or ventricular septum or the left or right ventricular outflow tract. Structures of the ear, the skin or the inner organs can also be generated therewith. The constructs according to the invention can also be used for in vitro pre-conditioning, for example in tissue transplantation in burn patients, etc. An aspect of the present invention is thus directed to a method for the transplantation of an acellular construct into an individual including the step of implantation of a bioartificial and acellular fibrin-based construct according to the invention.

Figure 1:
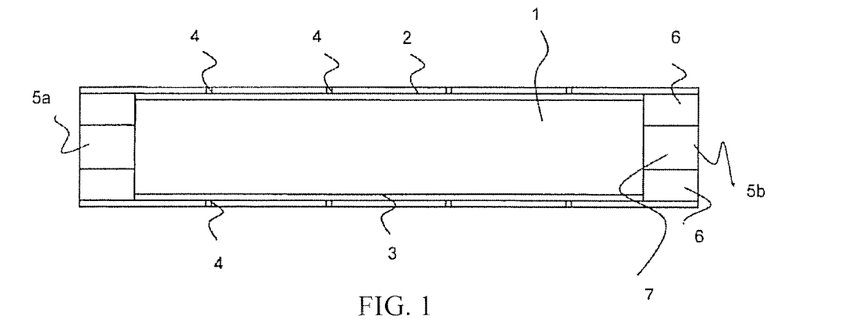
FIG. 1 shows a rotating mould according to some embodiments of the disclosure.

FIG. 1 shows a rotating mould 1 that can be used according to the invention. Here, the rotating mould 1 comprises an outer shell 2, which for example can be configured in the form of a metal tube. The inner mould 3 is configured such that the fibrin construct does not adhere to it. For example, the inner mould 3 can be composed of two Teflon half shells. The size of the internal mould 3 determines the external diameter of the fibrin construct to be produced.

In an embodiment, the outer shell 2 can have at least one through hole 4. These through holes 4 in the outer shell 2 of the mould 1 allow the liquid to be guided out of the mould 1 on rotation.

Furthermore, the rotating mould 1 has a collar 5a, 5b at both ends, also referred to as a cuff. This collar is configured such that it is permeable to liquids in the central area and to gases over its entire area. The collars 5a, 5b with a plurality of sections 6, 7 determine the liquid level of the introduced fibrinogen and thrombin suspension.

Figure 2:
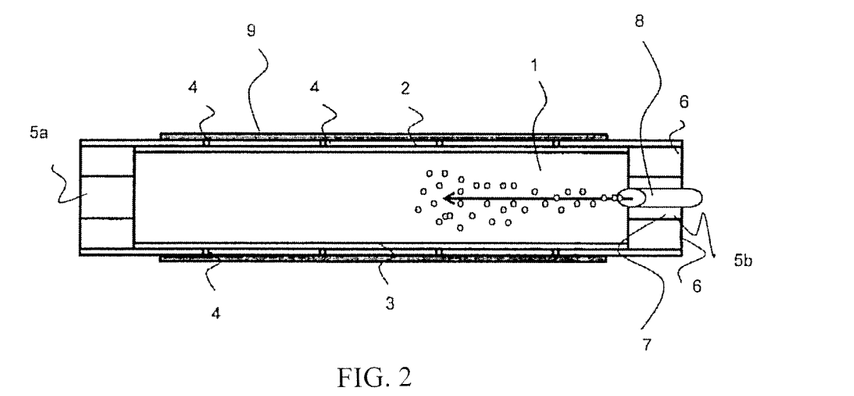
FIG. 2 shows the introduction of the solution containing fibrinogen and thrombin according to some embodiments of the disclosure.

FIG. 2 shows the introduction of the solution containing fibrinogen and thrombin. For this purpose, the solution or the suspension is applied through the collar 5 using an applicator 8. In this case, the through holes 4 are covered with a cover 9 at the beginning of rotation. This cover 9 can be in the form of a detachable film, etc., for example. Alternatively, the through holes can be covered with a semipermeable material as a cover 9, such as a non-woven fabric. This semipermeable material allows separation of the liquid, while the fibrinogen and the thrombin remain in the mould.

Figure 3:
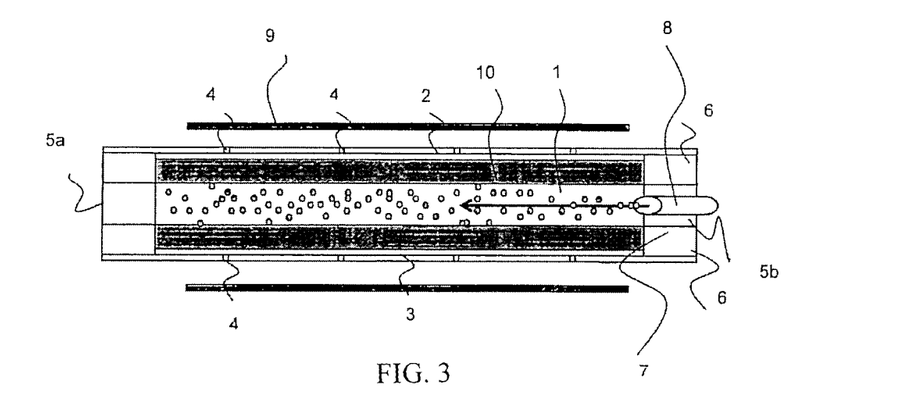
FIG. 3 shows the application of the fibrinogen-containing and thrombin-containing solution through the collar using the applicator according to some embodiments of the disclosure.

In FIG. 3, the fibrinogen-containing and thrombin-containing solution is further applied through the collar 5 using the applicator 8. The cover 9 was optionally removed from the through holes 4 in order to allow the liquid to be drawn off. In use of a semipermeable material, the cover remains on the outer side. The fibrinogen suspension containing the thrombin is ordinarily highly aqueous, and the low concentration of the activating thrombin causes polymerisation to take place slowly and allows uniform distribution in the rotating mould. The cover 9, if necessary, is e.g. opened when the mould is half filled. The fibrin construct 10 is formed on the internal mould 3. If the cover 9 is a semipermeable material, this remains on the outer side.

Figure 4:
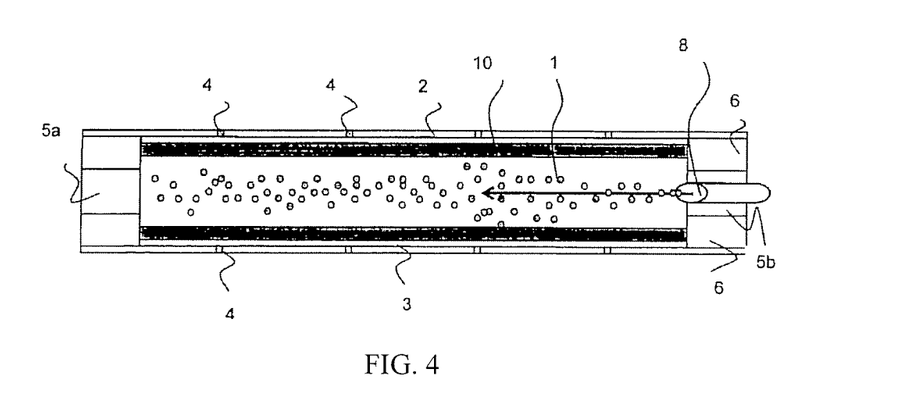
FIG. 4 shows the application of the fibrinogen/thrombin-containing solution through the collar using the applicator according to some embodiments of the disclosure.

The fibrinogen/thrombin-containing solution is further applied through the collar 5 using the applicator 8, as shown in FIG. 4. The excess liquid can escape through the through holes 4, with already-polymerised fibrin 10 acting as a filter and holding back further fibrin and fibrinogen, so that only liquid, i.e. the aqueous solvent, is withdrawn via the through holes 4. The liquid is pressed out of the mould by the rotation, while the polymerising fibrin is compressed by the centrifugal forces.

Figure 5A:
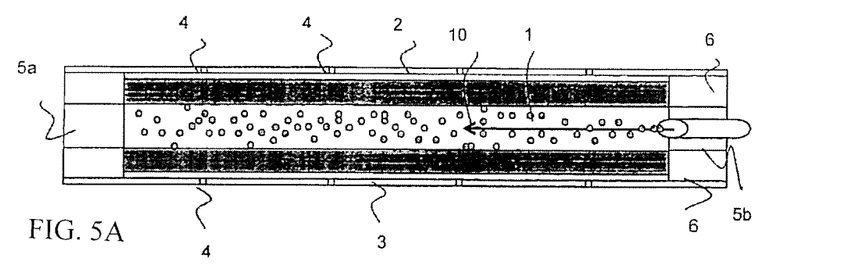
FIG. 5A-B show the compression of the polymerising fibrin construct. (A) shows the suspension containing thrombin and fibrinogen further introduced during the rotational method. (B) shows compression of the fibrin matrix.

FIG. 5 further shows the compression of the polymerising fibrin construct. The upper portion of FIG. 5 shows the suspension containing thrombin and fibrinogen further introduced during the rotational method, which thus forms the liquid construct. This suspension is poured in until the area 6 of the collar that only allows gas to pass through is completely filled.

Figure 5B:
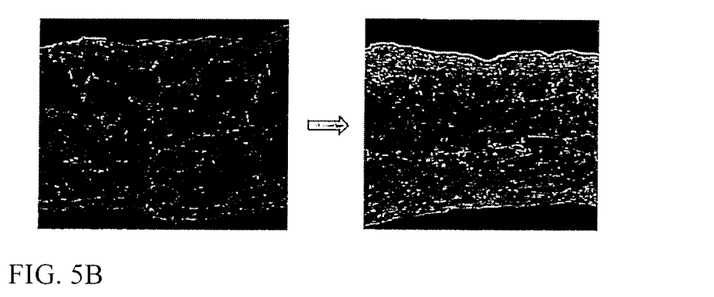

Compression of the fibrin matrix 10 is shown in the lower portion of FIG. 5. The centrifugal forces compress the polymerised fibrin onto the wall of the mould 1 while liquid is pressed from the mould. The compression of the fibrin matrix can be seen in the right-hand figure.

The construct formed in this manner can then be removed from the rotating mould 1 as a hollow body. A protocol for carrying out the method according to the invention with such a rotating mould is presented in the examples.

In the following, the invention is explained in further detail by means of examples, without being limited thereto:

Example 1

Protocol for Generating a Bioartificial Vascular Graft by Means of a Rotating Mould (Centrifugal Casting):

1. Precipitation of the fibrinogen from plasma or donor blood by means of a freezing/thawing cycle (cryoprecipitation) according to known methods. Alternatively, this can be carried out by adding ethanol (ethanol precipitation). Ordinarily, 8-10 ml of fibrinogen preparation are precipitated from 50 ml of plasma.

2. Resuspension of the separated fibrinogen in the separated plasma in a low concentration (10 to at most 20 mg/ml).

The fibrinogen is present in the plasma in relatively highly diluted form (10-20 mg/ml), so that only a comparatively high-concentration thrombin component can be added in order to cause the fibrinogen to harden. All previous approaches in the prior art attempted to control the rate of hardening of the fibrinogen via the concentration of thrombin. However, it was found that the approach used here is advantageous with respect to more uniform mixing and distribution of the mixture in the rotating mould.

3. Application of the fibrinogen preparation to the mould simultaneously with a thrombin solution at a 6:1 ratio. 1 ml of the thrombin component is composed of:
   850 units of thrombin in 850 µl of CaCl solution (40 mmol/l)
   100 µl of CaCl (1 M)
   50 µl of aprotinin solution (250,000 KIU/ml)

4. Because of the strong dilution of the fibrinogen preparation, this solution is highly aqueous, hardens slowly, and is therefore favourably distributed in the rotating mould. In this approach, therefore, application can be carried out from one end of the rotating mould. It is also possible to produce constructs of longer segments of at least 20 cm and segments with an internal diameter of 2 mm.

5. Application of the solutions from one end. The mould is already initially rotating at 10,000-15,000 rpm (depending on the diameter of the mould, up to 900 g). The through holes in the mould, via which excess liquid is pressed from the mould during centrifugation, are first closed. The mould is filled to 40% of its volume.

6. Centrifugation at 10,000-15,000 rpm for 2 min. The through holes in the mould are then re-opened. If applicable, the mold must be briefly stopped for this purpose in order to remove the cover of the through holes.

7. After this, further application of the fibrinogen and thrombin solutions (6:1 ratio) during rotation of the mould at 10,000-15,000 rpm.

8. Application of a total of 8-10 ml of the fibrinogen preparation (150-200 mg of fibrinogen) separated from 50 ml of plasma.

9. After complete application (total duration approx. 5 min), further rotation of the mould for another 15 min.

10. For heparin coating of the surface, 1 ml of thrombin solution is then applied to the further rotating mould. The solution is composed of:
    850 units of thrombin in 850 µl of CaCl-solution (40 mmol/l)
    150 µl CaCl (1 M)

11. After further rotation of the mould for 5 min, application of 1 ml of heparin solution (5,000 units of heparin per ml).

12. Further rotation of the mould for another 15 min.

13. Stopping of rotation and removal of the container from the mould.

Figure 7A:
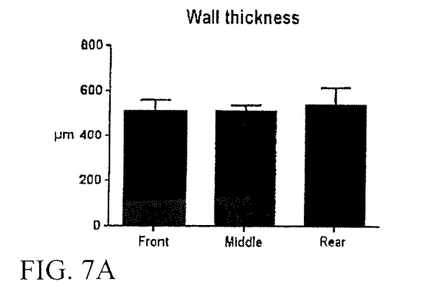
FIG. 7A-C shows the (A) wall thickness, (B) maximum wall tension, and (C) maximum burst pressure of a construct.
Figure 7B:
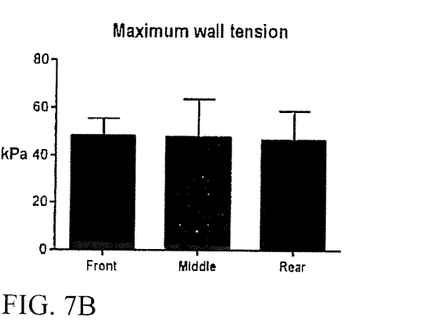
Figure 7C:
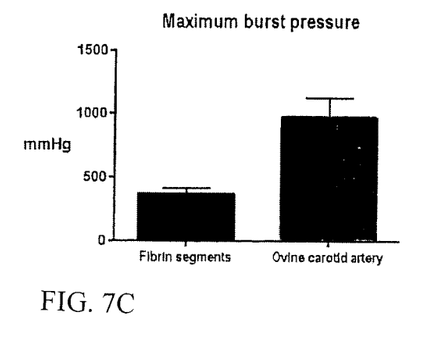

FIG. 7 shows the properties of the construct produced in this manner. Because of the temporary closure of the through holes, fibrin that is already applied and polymerised on the wall of the mould acts as a filter for further fibrinogen applied subsequently. By means of this method, uniform distribution of the fibrin (a) and uniform biomechanical stability of the wall (b) are achieved. Up to 250 mg of fibrinogen can be applied in a rotating mould with a length of 100 mm and a diameter of 6 mm using this method. This makes it possible to generate fibrin segments having a maximum burst strength of approx. 400 mmHg (c).

Example 2

Alternate Protocol

1. Structure of a rotating mould composed of an outer brass shell fitting into two half shells of Teflon. Each of the two ends is narrowed using a Teflon cuff, each of which has a central through hole 3 mm in diameter, in order to prevent loss of the fibrin at the ends. External application of Leukopor (BSN Medical GmbH, Hamburg) to the brass tube of the mould.

2. The mould prepared in this manner is slid into the connector of an electric motor by means of which the mould is rotated.

3. The applicator is composed of a steel tube with a diameter of 2.5 mm and two silicone tubes with a diameter of 1 mm inserted into one another such that the end of the tubes extends approx. 2 mm beyond the end of the steel tube. Each of the other ends of the silicone tube is attached to a syringe pump via Luer lock connectors.

4. Fixation of the applicator on an adjustable electrically operated slide so that the end of the applicator extends freely to a length corresponding to that of the mould. The free end can then be slid into the mould by means of the electrically operated slide.

5. Aspiration of the fibrinogen preparation and the activator solution respectively into one syringe, said syringes being connected to silicone tubes in the applicator. Use of a purified fibrinogen preparation (cf. Example 3) with a concentration of 40-60 mg/ml. The concentration of the thrombin in the activator solution is 100 units per ml.

6. Rotation of the mould at 5,000-8,000 revolutions per minute (rpm) while the applicator is slid into the mould from one end at a feed rate of 2 (1-3) mm per sec.

7. Multiple repetitions of step 6.

Example 3

Purification/Washing of Fibrinogen

1. Freezing of obtained plasma at −20° C. for at least 24 hr.

2. Thawing of the plasma at room temperature.

3. Centrifugation of the completely thawed plasma at 200-300 g for 3 min.

4. Complete removal of the plasma supernatant and resuspension of the fibrinogen/protein pellets from 50 ml plasma in 20 ml of water for injection, which is frozen for at least 24 hr at −20° C.

5. The frozen fibrinogen/protein suspension is thawed at room temperature. The completely thawed suspension is centrifuged at 200-300 g for 3 min.

6. Complete removal of the supernatant and resuspension of the still aqueous fibrinogen pellets in the water bath at 37° C. without further addition of liquid.

Example 4

Protocol for Generating a Tissue Patch in the Pressure Vessel

The fibrin-containing and the thrombin-containing solution are simultaneously poured under simultaneous mixing in a corresponding applicator into a mould such that the ratio of thrombin (units per ml) to fibrinogen (mg per ml) is in a range of 1:1 to 10:1.

The size and shape of the mould are variable. The mould allows the supply of compressed air up to a pressure of 15 bar. A porous base plate of the mould allows liquid to escape during pressurisation.

In an embodiment, pressurisation takes place during polymerisation of the fibrin. In another embodiment, pressurisation is essentially carried out after polymerisation of the fibrin.

Pressurisation takes place in a planar manner by means of compressed air on the surface of the applied compositions, with a relative pressure of at least 1 bar, such as at least 5 bar or at least 10 bar, i.e. at least 15 bar for 10 min, such as least 20 min, e.g. at least 60 min.

After pressurisation, the finished fibrin matrix is removed from the base plate.

Example 5

The fibrin segments are dehydrated for storage. This can be carried out by cryopreservation, freeze-drying or vacuum-drying or simple drying in dry air.

Example protocol for dehydration of a fibrin segment in dry air:

1. The fibrin segment generated in a rotating mould is threaded onto a trocar (diameter of 3 mm in the example).
2. The trocar and the fibrin segment are placed upright in a container filled at the bottom with 20 g of salt.
3. Changing of the container filled with salt every 24 hr.
4. Dehydration for 72 hr.
5. Storage in a sterile container (not filled with salt) at room temperature.

Figure 8A:
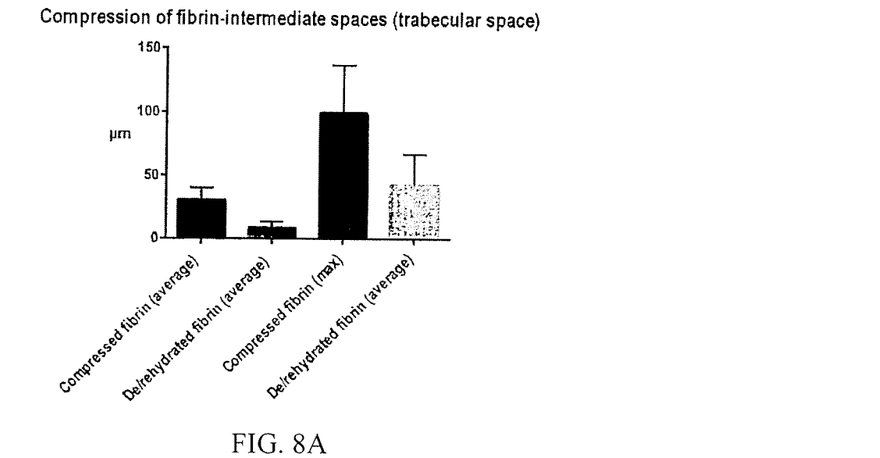
FIG. 8A-C shows (A) the compression of the trabecular space, (B) cross-links, and (C) maximum burst pressure after rehydration.
Figure 8B:
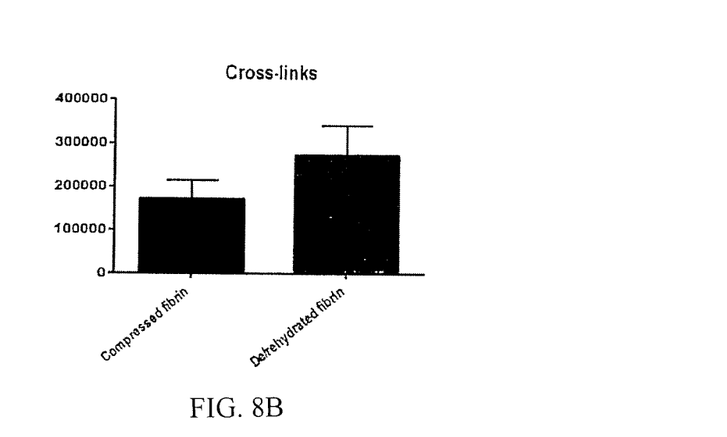

For implantation, the dehydrated fibrin segments are then rehydrated in physiological saline. Alternatively, other liquids, such as calcium chloride solution, can be used. The dehydration causes further compression of the fibrin, with a considerable improvement in its biomechanical properties, which are retained or only partially lost after rehydration (FIG. 8). The dehydration/drying of the fibrin causes it to be further compressed. Analysis of the fibrin structure by means of histological sections showed that after dehydration and subsequent rehydration, the intermediate spaces (trabecular space) between the fibrin fibrils decreased significantly, and this applied both to the average and the maximum size of the intermediate spaces (a). At the same time, the number of cross-links increased significantly compared to compressed fibrin that was not dehydrated (b).

Figure 8C:
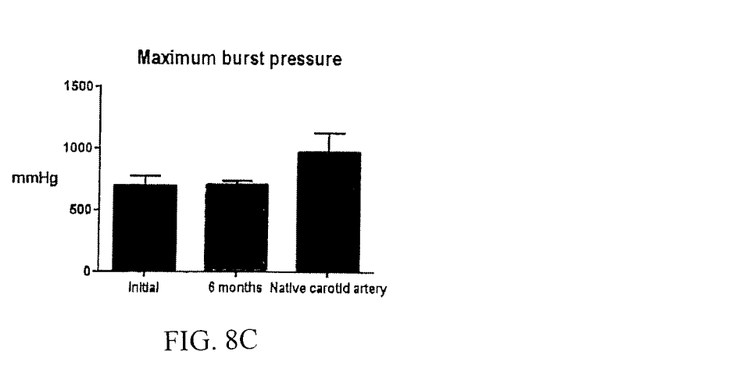

Accordingly, de/rehydration also further increases the stability of the segments. This makes it possible to produce, from 250 mg of fibrinogen, fibrin segments having a burst strength of approx. 700 mmHg (c).

Figure 9:
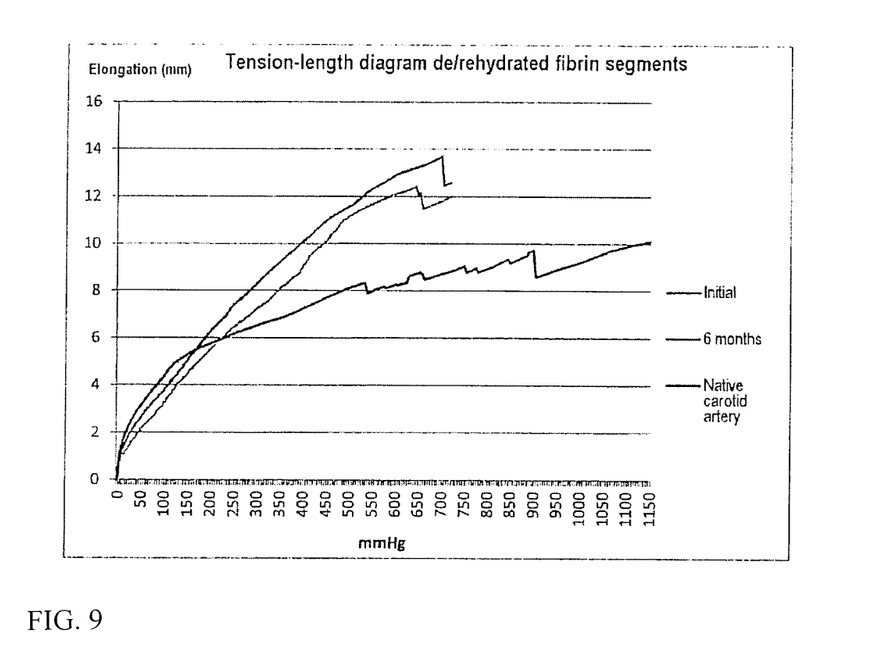
FIG. 9 shows a tension-length diagram during storage.

Therefore, in the pressure range of up to 200 mmHg, fibrin even shows biomechanical properties that are comparable to those of a native artery with respect to elasticity. We have been able to demonstrate to date that it is possible to store dehydrated fibrin segments for at least 6 months at room temperature (FIG. 9). A significantly longer shelf life is to be expected at 4° C.

The dehydration and subsequent rehydration produces an improvement in the biomechanical properties of the fibrin segments. Up to a pressure of 200 mmHg, these fibrin segments even show elasticity that is comparable to that of a native carotid artery. These properties are retained even after six-month storage at room temperature, cf. FIG. 9.

Colonisation of an acellular substrate structure with autologous (=endogenous) cells of the recipient has become established in the last few decades as a basic principle of tissue engineering. The purpose of this is to cause the implants to be recognized by the body as endogenous so that they can undergo endogenous remodeling. In cardiovascular implants, colonisation of the surface with endothelial cells is also intended to reduce the thrombogenicity of the implant. In an in vivo study, uncolonised acellular fibrin segments were implanted in sheep as carotid artery replacements. On explantation of the segments after 6 months, all of the implants remained patent. Histological examination of the explanted fibrin segments showed that they had undergone pronounced remodeling in vivo after implantation. Cells from surrounding tissues (including endothelial cells and smooth muscle cells) migrated into the fibrin and arranged themselves according to the structure of a vessel wall. The lumen was covered with an endothelial layer. The fibrin was replaced by other matrix proteins such as collagen. These results shown that no colonisation of the fibrin segments prior to their implantation as vascular grafts is required. Only heparin was bonded to the luminal surface in order to reduce thrombogenicity.

Dispensing with colonisation of the fibrin segments offers numerous advantages:
  The fibrin segments can be produced more easily because the steps otherwise required for colonisation are omitted.
  The fibrin segments are no longer individualized, i.e. they are no longer individually produced for a recipient.
  The acellular fibrin can be stored.
  Compared to the current state of the art, the segments must be subdivided into two groups:
  Synthetic vascular grafts (e.g. composed of the materials Dacron or polytetrafluoroethylene).
  Colonised bioartificial vascular graft segments.

Compared to synthetic vascular grafts, the developed acellular fibrin segments have the advantage of undergoing remodeling in vivo after implantation, i.e. endogenous reconstruction and repair mechanisms. Ideally, this allows a long-term course such as that of a native artery to be expected. The major advantage over colonised bioartificial vascular graft segments is shelf life. In this manner, a stock of vascular graft segments can be produced and stored locally. This is a decisive advantage with respect to clinical use.

Example 6

Comparison of Static Construct and Construct According to the Invention

Figure 6A:
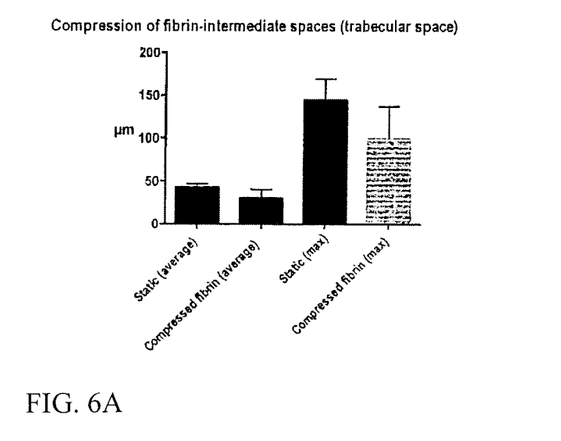
FIG. 6A-B shows the results of a biomechanical stability test related to (A) the trabecular space and (B) cross-linking among fibrils.
Figure 6B:
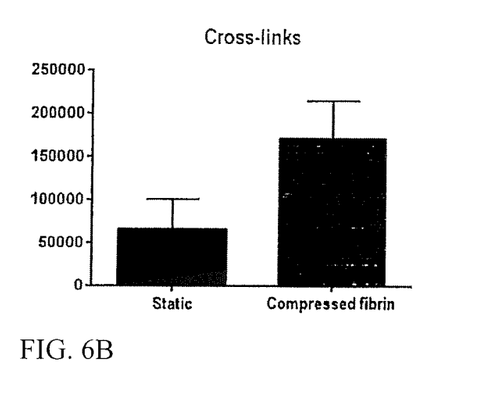

Biomechanical stability was tested using the software BoneJ/ImageJ, www.bonej.org. The tests were conducted on tissue sections. The results are shown in FIG. 6. The centrifugal forces in the rotating mould lead to compression of the applied fibrin (compressed fibrin) compared to a fibrin matrix generated under static conditions (static). The intermediate spaces between the fibrin fibrils (trabecular space) are smaller both in average and maximum size (a). This leads to increased cross-linking among the fibrils (b).

Example 7

Biomechanical Properties of Fibrin Patches

The fibrin patches produced according to Example 2 were tested for their biomechanical properties. For this purpose, pressurised fibrin patches were tested together with non-pressurised fibrin patches, wherein pressurisation was carried out at 6 bar for 20 min.

Figure 10:
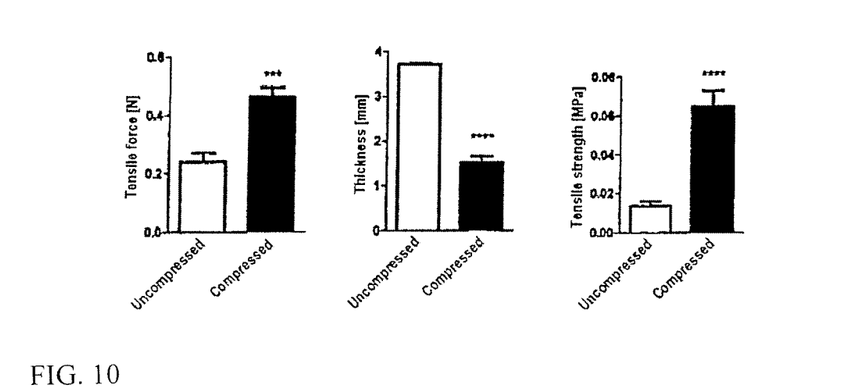
FIG. 10 shows the effect of compression with respect to tensile force, density and tensile strength.

FIG. 10 shows the effect of compression with respect to tensile force, density and tensile strength. It was possible to achieve improved tensile force, and more particularly improved tensile strength (almost quadrupled), compared to the uncompressed fibrin patches. Further tests demonstrated that the patches showed increasing tensile force with rising fibrin concentration.

In this connection, the fibrin patches tested were cast simultaneously, some being polymerized without pressurisation and others with pressurisation, wherein it was possible for both types of patches for liquid to be discharged.

The invention claimed is:

1. Method for producing a fibrin-based bioartificial and acellular construct, comprising the following steps:
   provision of a fibrinogen-containing and cell-free composition;
   provision of a thrombin-containing and cell-free composition;
   application of the fibrinogen-containing cell-free and the thrombin-containing cell-free compositions to a surface;
   pressurisation of the mixture of compositions applied to the surface at least until the fibrin formation is essentially completed; and
   removal of the fibrin-based acellular bioartificial construct from the surface, wherein application of the compositions takes place in a rotating hollow body and pressurization takes place by rotation of the hollow body and wherein during the rotation, liquid is discharged via holes present in the hollow body and through a semipermeable membrane arranged on an outside surface of the hollow body.

2. Method according to claim 1, wherein rotation of the hollow body takes place during application of the compositions and the fibrin formation takes place such that an amount of at least 600 g is present on the surface.

3. Method according to claim 1, wherein the compositions, together or separately, are applied multiple times.

4. Method according to claim 1, wherein a thrombin-containing composition is first applied, followed by a heparin-containing composition, as compositions forming an uppermost layer.

5. Method according to claim 1, wherein the fibrinogen-containing composition is a composition in which the fibrinogen is obtained from plasma.

6. Method according to claim 1, wherein the compositions applied to the surface form a layer having a thickness of at least 0.5 mm.

7. The method according to claim 6, wherein the layer has a thickness of at least 1 mm.

8. The method according to claim 7, wherein the layer has a thickness of at least 1.5 mm.

9. Method according to claim 1, wherein a plurality of layers is applied successively and wherein these layers can contain different proportions of the thrombin-containing composition and the fibrinogen-containing composition and/or wherein at least one fibrin-containing layer is applied and at least one non-fibrin-containing layer is applied.

10. The method according to claim 9, wherein the non-fibrin containing layer comprises other biological materials or synthetic materials.

11. Method according to claim 1, wherein the fibrinogen-containing composition is a solution that contains the fibrinogen in a concentration of at most 60 mg/ml.

12. The method according to claim 11, wherein the solution contains the fibrinogen in a concentration of at most 20 mg/ml.

13. Method for producing a fibrin-based bioartificial and acellular construct, comprising the following steps:
   provision of a fibrinogen-containing and cell-free composition;
   provision of a thrombin-containing and cell-free composition;
   application of the fibrinogen-containing cell-free and the thrombin-containing cell-free compositions to a surface;
   pressurisation of the mixture of compositions applied to the surface at least until the fibrin formation is essentially completed; and
   removal of the fibrin-based acellular bioartificial construct from the surface, wherein application of the compositions takes place in a rotating hollow body and pressurization takes place by rotation of the hollow body, wherein during the rotation, liquid is discharged via holes present in the hollow body and through a semipermeable membrane, wherein the hollow body has a collar at either end of the hollow body through which the compositions can be introduced, and wherein the collar is permeable to gases over its entire area.

* * * * *